United States Patent [19]

Lissant

[11] 4,040,857
[45] Aug. 9, 1977

[54] NON-NEWTONIAN PHARMACEUTICAL COMPOSITIONS

[75] Inventor: Kenneth J. Lissant, St. Louis, Mo.

[73] Assignee: Petrolite Corporation, St. Louis, Mo.

[21] Appl. No.: 551,727

[22] Filed: Feb. 21, 1975

Related U.S. Application Data

[60] Division of Ser. No. 201,562, Nov. 23, 1971, Pat. No. 3,892,881, Continuation-in-part of Ser. No. 784,905, Dec. 18, 1968, abandoned.

[51] Int. Cl.$^2$ .................... A01N 9/04; B01J 13/00; C08L 91/00
[52] U.S. Cl. .................... 106/243; 106/285; 252/316; 424/168; 424/170
[58] Field of Search .................... 106/243, 285; 260/429.3, 414; 252/316; 424/168–172

[56] References Cited

U.S. PATENT DOCUMENTS

| | | | |
|---|---|---|---|
| 2,529,461 | 11/1950 | Schneiderwirth | 252/316 |
| 3,507,806 | 4/1970 | Barker et al. | 252/316 |
| 3,635,834 | 1/1972 | Cilento | 252/314 |
| 3,740,421 | 6/1973 | Schmolka | 252/316 |

OTHER PUBLICATIONS

"Thixotropic Mineral Gels and Their Therapeutic Possibilities" Schneiderwirth et al., June 7, 1947.
Chem. Abst. 51: 10,180c 1957.
Chem. Abst. 53: 6547g 1957.

*Primary Examiner*—Theodore Morris
*Attorney, Agent, or Firm*—Sidney B. Ring; Hyman F. Glass

[57] ABSTRACT

Non-Newtonian cosmetic, nutritive and pharmaceutical compositions as exemplified by thixotropic high internal phase ratio emulsions of cosmetic, nutritive and pharmaceutical agents.

10 Claims, No Drawings

NON-NEWTONIAN PHARMACEUTICAL COMPOSITIONS

This application is a division of Ser. No. 201,562, filed Nov. 23, 1971, now U.S. Pat. No. 3,892,881, issued July 1, 1975, which is a continuation-in-part of Application Ser. No. 784,905, filed on Dec. 18, 1968, now abandoned.

This invention relates to non-Newtonian cosmetic, nutritive and pharmaceutical compositions as exemplified by thixotropic high internal phase ratio emulsions incorporating cosmetic, nutritive and pharmaceutical agents therein.

Although emulsions are widely used in cosmetic, nutritive and pharmaceutical applications, where such emulsions are used they have been of the low or medium internal phase ratio type. Furthermore, the art has taught that such emulsions are unstable when they have an internal phase in excess of 75%.

I have now discovered non-Newtonian compositions which are suitable for cosmetic, nutritive and pharmaceutical uses.

These non-Newtonian cosmetic, nutritive and pharmaceutical preparations are best exemplified by stable high internal phase ratio emulsions. High internal phase ratio emulsions possess radically different properties from those of the low or medium internal phase ratio types. Specifically, they are non-Newtonian in nature exhibiting a yield value phenomenon and a decrease in the effective viscosity with shear rate. In contrast to gels which require significant time periods to recover their body when subject to shear, high internal phase ratio emulsions recover to high viscosities almost instantaneously.

The use of high internal phase ratio emulsions of the present invention presents many advantages in cosmetic, nutritive and pharmaceutical formulations. Finely divided solids or, indeed, coarse solids may be dispersed in the internal phase of a high internal phase ratio emulsion and thereby are suspended stably for extended periods of time. It is thus possible to take formulations which normally require either thickening agents to keep the solids suspended or vigorous agitation just prior to application and convert them to stable, non-settling formulations without the incorporation of large amounts of immiscible material. For instance, a water-based cosmetic formulation containing pigments and typically used as a body or leg make-up may be formulated into a water-in-oil high internal phase ratio emulsion employing approximately 2% by volume of bland oily external phase to produce a formulation possessing all the advantages of the original material but being non-settling in character.

Since high internal phase ratio emulsions are already super-creamed, they do not tend to separate on storage and therefore exhibit superior stability without the necessity of producing extremely fine particle size.

Because of the inherent high viscosity of the high internal phase ratio emulsion formulations may be produced which possess the desired viscosity properties without the incorporation of film-forming thickeners or gelling agents. These formulations spread well but do not leave behind a sticky or adherent solid film upon the evaporation or absorption of the liquid ingredients.

Many medicinally active materials available at the present time must be applied in very small amounts. Where the active ingredient is soluble in either water or an acceptable oily phase, this can be done by preparing dilute solutions. However, by using a concentrated solution as the external phase an immiscible liquid may be used as a diluent. In many instances where medications are to be applied to the skin, they are more readily absorbed if incorporated in an oily medium. High internal phase ratio formulations of the water-in-oil type may be used to produce effectively dilute formulations wherein the oil phase comes in contact with the skin allowing good penetration without having to penetrate a previously laid down water layer as is now the case with low internal phase ratio oil-in-water emulsions.

Medicinal or nutritive formulations intended for oral application may be prepared of either the oil-in-water or water-in-oil type. Aqueous solutions of materials possessing an undesirable taste may be incorporated as the internal phase in a high internal phase ratio water-in-oil emulsion wherein a bland edible oil is used to mask the flavor. Similarly, oily compositions which are usually unpalatable may be used as the internal phase of an oil-in-water emulsion with greatly improved flavor and mouth feel.

By "non-Newtonian" I mean a fluid of thixotropic or pseudo-plastic character. By definition, these fluids possess the property of exhibiting variable apparent viscosity when the shear rate is varied. Stated another way, when these fluids are pumped at low shear rates, they behave as though they are extremely viscous fluids; but as the pumping rate is increased and concomitantly the shear rate increases, the fluids appear to "shear thin" and then behave as though they have low viscosities.

I have particularly found, however, that the use of emulsions, and specifically high-internal-phase-ratio emulsions, i.e. where the internal phase is a major part of the emulsion, are particularly well suited for this purpose, since from an economic standpoint, large volumes of emulsion may be formulated with inexpensive major constituents thereby providing inexpensive fluids.

The non-Newtonian fluids employed in the practice of this invention, however, are characterized by the fact that when at rest or under low shear conditions they behave like elastic solids or extremely viscous liquids; but when subjected to moderate shear rates, such as are encountered in pumping through pipes at practical, but not extremely rapid rates, the fluids behave as though they were low viscosity media. These emulsions contain an internal phase which is the major part of the emulsions; for example, at least about 60%, such as at least about 80%, but preferably in excess of about 90%, by volume, and often 95% or higher.

High internal phase emulsions of the type which can be employed in this invention are those disclosed in the following U.S. Pat. Nos.

| | | |
|---|---|---|
| 3,565,817 | February 23, 1971 | Continuous Process for the Preparation of emulsions |
| 3,539,406 | November 10, 1970 | Essentially Non-Aqueous Emulsions |
| 3,490,237 | January 20, 1970 | Thixotropic Oil-in-Water Emulsion Fuels |
| 3,396,537 | August 13, 1968 | Hybrid Fuel II |
| 3,352,109 | November 14, 1967 | Hybrid Thixotropic Rocket and Jet Fuels Comprising Oil in Water Emulsions |

The thixotropic emulsions of this invention, which have the characteristics of solids at rest and liquids when force is exerted on them, have the following advantages:

1. Nonadhesive — They do not tend to stick to the sides of the container or system.
2. Viscosity — The apparent rest viscosity is greater than 1000 cps, generally in the range of 10,000 – 100,000 or greater, preferably 50,000 – 100,000 cps or more. However, under low shear, they will flow with a viscosity approaching that of the liquid phases. On removal of shear, the recovery to original apparent rest viscosity is nearly instantaneous. The hysteresis loop is very small.
3. *Temperature Stability* — Increased temperature has little effect on viscosity until the critical stability temperature is reached at which point the emulsion breaks into its liquid components. This permits a wide temperature range of use.
4. *Shear Stability* — Emulsions may be subjected repeatedly to shear without degradation so long as the critical shear point is not reached. At this point the emulsion breaks. However, the critical shear point is sufficiently high to permit high normal pumping and handling.
5. *Quality Control* — With these emulsions it is easy to reproduce batches with identical properties due to the absence of any "gel" structure.
6. *Solids Contents* — Emulsions will flow well even with high solids content since they have a broad range between rest viscosity and viscosity under modest shear.

In contrast to very high volume percent solid loading in gels or slurries which result in a "putty," these emulsions can suspend such solids in the internal phase while allowing the external phase to govern "flowability."

The above patents, which are by reference incorporated into the present application, relate to stable, viscous thixotropic emulsions and to the uses, preparation, etc., of these emulsions.

Whether an oil external or an aqueous external phase is employed in preparing these emulsions will depend on the particular system in which it is employed.

Thus, the emulsions employed in this invention include:

1. Oil-in-water emulsions
2. Water-in-oil emulsions
3. The above emulsions of (1) and (2) where waterlike substances are employed in place of water as described in said U.S. Pat. No. 3,539,406. Said substances are nonaqueous non-oily substances and include ethylene glycol, diethylene glycol, propylene glycol and dipropylene glycol. Thus, the emulsions employed in this invention are oil-in-non-oil emulsions or non-oil-in-oil emulsions, water of course being included as a non-oil.
4. Emulsions prepared by a continuous method, as described in application Ser. No. 411,103, filed on Nov. 13, 1964, and now abandoned, and in its continuation-in-part Application Ser. No. 753,340, filed on Aug. 15, 1968, now U.S. Pat. No. 3,565,817. In that Application Ser. No. 411,103 it is stated as follows:

"This invention relates to high internal phase emulsions and to methods for their preparation, and the like. More particularly this invention relates to a method for the continuous production of high internal phase emulsions which is characterized by introducing, with sufficient agitation, into a preformed emulsion both the internal and the external phase of the emulsion, in the presence of the emulsifier, in such proportions so as to produce the desired emulsion; the character of said preformed emulsion approximating that of the desired emulsion; and withdrawing the prepared emulsion at the desired rate.

"Classically an emulsion is defined as a continuous liqui phase in which is dispersed a second, discontinuous liquid, phase. It is also well known that when an immiscible liquid phase is introduced into a second liquid phase with agitation, the introduced phase disperses into discrete droplets. If two pure liquid phases are used, the droplets will begin to coalesce as soon as agitation is stopped and will separate into two discrete phases. If approximate surface active materials or emulsifiers are present in the system, coalescence will be prevented, and when agitation is stopped, a layer of droplets of the dispersed phase will form. This is known as 'creaming'. However, if the droplets of internal phase are made small enough so that thermal and Brownian forces overcome the settling effect of the gravity field then a 'stable' emulsion results.

"Practically all emulsions are made on a batch-wise basis. That is, an approximate amount of the external phase is placed in a mixing vessel and the internal phase is added, a little at a time, until the desired amount of internal phase has been introduced. Provision is made for sufficient agitation so that the necessary degree of subdivision is obtained. This often requires devices capable of producing high shear rates, such as high speed impellors, colloid mills, etc. Recently cavitation produced by ultrasonics has also been used as a means of producing high shear rates.

"Emulsions containing 10% to 30% internal phase by volume have been made on a semi-continuous basis. In this case the internal phase is fed into the external phase and mixed to form a loose dispersion. The dispersion is then fed to a higher shear device and the droplet size reduced until stability is obtained. However, as the volume of internal phase approaches the volume of external phase, it becomes increasingly difficult to be sure that the dispersion will form with the proper external phase. When the volume of internal phase is greater than that of the external phase, it is only in very specific cases and with great difficulty that a proper emulsion can be made by simple mixing.

"Emulsions in which the volume of internal phase exceeds the volume of external phase, when required commercially, are made on a batch basis. The procedure is to place the external phase in a mixer, add the emulsifying agent, and then add the internal phase slowly with vigorous mixing. Sometimes the internal phase is added slowly but continuously. Usually it is added in increments and mixed well between additions. The process is however a batch process.

"It has been suggested that high internal phase ratio emulsions can be made continuously by mixing some of the internal phase with an excess of the external phase and then transferring this pre-mix to another chamber where more internal phase is added. This partial mix is then transferred to another chamber where more internal phase is added. Enough stages are provided to obtain the desired ratio. In actual practice this method is difficult to accomplish. It requires separate mixers, pumps, and proportioning equipment at each stage and the stages have to be interlocked to assure uniformity of product.

"I have now discovered that high internal phase ratio emulsions can be continuously made by (1) preparing a preformed emulsion of approximately the same character as the desired emulsion, (2) introducing, with sufficient agitation, into the preformed emulsion, both the internal and external phases of the emulsion in such proportions so as to produce the desired emulsion, and (3) withdrawing the prepared emulsion at the desired rate.

"Examples of internal phase emulsions which can be continuously prepared according to this invention are described in application Ser. No. 286,877, filed May 20, 1963 (now abandoned) and in applications Ser. No. 302,001 (now 3,396,537) and Ser. No. 302,177, both filed Aug. 14, 1963 (302,177 now being abandoned and being the parent of its continuation application Ser. No. 547,581, filed on May 4, 1966, now U.S. Pat. No. 3,352,109).

"These applications are by reference incorporated into the present application and are part of the present disclosure as if specifically described herein."

Pertinent examples of the emulsions set forth in said abandoned Application Ser. Nos. 286,877 and 302,177 and also in said 302,001, which become said U.S. Pat. No. 3,396,537, were later set forth in said abandoned Application Ser. No. 411,103, as shall hereinafter become obvious.

Then, in that said applicaton Ser. No. 411,103 it is further stated as follows:

"In the practice of my invention I have found that high internal phase ratio emulsions can be made continuously in simple, compact equipment.

"An example of an apparatus which can be used in the practice of my invention consists of a mixing chamber equipped with mixing blades of such a configuration that the highly thixotropic emulsion is completely mixed without excessive dead spots, inlet ports for the internal and external phase and an exit port for the finished emulsion. In operation the equipment is first filled with an emulsion approximating that of the desired composition and then the stirring device is activated. Simultaneous injection of the internal and external phases is then begun. As the mixer incorporates the new material into the emulsion in the chamber, finished emulsion is displaced from the exit port. The process may be envisioned as though a small batch of emulsion has been made containing X amount of external phase and Y amount of internal phase, the ratio Y/X being R. Now if a small amount, $p$, of external phase is added and the batch well mixed, a new emulsion with a slightly different ratio will result. Now if an amount of internal phase equal to $pR$ is added and mixed in one will have an emulsion of the same ratio as at the beginning but a larger volume by an amount $p$ plus $Rp$. If this amount of finished emulsion is now removed, one is back to the initial state in the mixing vessel.

"Although I do not wish to be bound by the theoretical considerations, my invention is based on the fact that I have found that $p$ and $Rp$ and the mixing time can be made very small. They can in essence approach a differential increment so that the process can be repeated successively and become continuous.

"The following examples ar presented for purposes of illustration and not of limitation.

"EXAMPLE 1

"The apparatus employed consists of a piece of glass pipe, 6 inches in diameter and 12 inches long. The ends of the pipe are closed by metallic plates held on by standard clamps and bolts and sealed with a gasket. In the plate forming the bottom end two holes are drilled, tapped and fitted with piping for the introduction of the internal and external phase. The top plate is drilled and fitted with a gland to admit a stirrer assembly and an exit port for the finished emulsion.

"The mixing assembly is driven by a motor turning at about 600 rpm. The mixing chamber holds about 5000 ml. of fluid. It is desired to make an emulsion with water as the external phase and kerosene as the internal phase. The phase ratio Y/X being 19/1. That is 95 parts of kerosene (Y) is emulsified in five parts of water (X) containing emulsifier.

"The external aqueous phase is made by dissolving 300 ml. of the emulsifier (n-decanol + PrO (1.96) + EtO (2.61)), parts by weight, in 1000 ml. of water. Two hundred ml. of this material is introduced into the mixing chamber. The mixer is started and 3800 ml. of kerosene, the internal phase, slowly pumped into the chamber with thorough mixing. The result is a smooth, white, highly thixotropic, $o/w$, emulsion. This is essentially a batch process. Now, with the mixing assembly turned on, feed pumps for both kerosene and water are started and set to feed five parts of aqueous phase to 95 part of kerosene. It is found that the chamber stayed full of smooth homogeneous emulsion and that emulsion is expelled from the exit line in a steady stream. A total of 38,000 ml. is put through the apparatus. Throughput is varied between 100 ml/min. and 900 ml/min. The output is sampled throughout the run and found to follow the input ratio in composition closely. At no time is the output found to be non-homogeneous.

"EXAMPLE 2

"This example illustrates that simultaneous addition of both phases from the very beginning does not form a stable emulsion. The same apparatus and components are employed as in Example 1. With the mixing chamber empty and the stirrer on, simultaneous pumping of both phases at the rate of 5 to 95 parts water to kerosene is begun. It is found that a loose dispersion of the aqueous phase in kerosene results which separates on standing. This dispersion is allowed to separate and then emulsified batchwise. When this preformed batch emulsion is present in the mixing chamber and pumping of both phases at the rate of 5 to 95 parts water to kerosene is resumed, a smooth emulsion results and the continuous production of an o/w emulsion is effected.

"EXAMPLE 3

"The procedure and apparatus of Example 1 is used except that the external phase is kerosene (5 parts) with a different emulsifier, namely octylphenol + EtO (0.69) by weight, and the internal phase is tap water (95 parts). Again production of emulsion is easily effected where the mixing chamber is intially filled with a w/o emulsion of the desired phase ratio.

"It is possible to vary the phase ratios and properties of the produced emulsion over wide limits simply by adjusting the emulsion in the chamber to the desired ratio and then adjuting the feed rates to correspond to this ratio. Internal to external phase volume ratios of 50% or greater can be prepared, for example from 50 to 98% or greater, such as 70 to 95%, advantageously 80 to 90%. The particular ratio will be determined by the desired application.

"Employing these techniques, the emulsions described in Ser. No. 286,877, filed May 20, 1963, now abandoned, and Ser. No. 302,001, now U.S. Pat. No.

3,396,537, and Ser. No. 302,177, the parent of Application Ser. No. 547,581, now U.S. Pat. No. 3,352,109, both filed Aug. 14, 1963, may be continuously prepared."

The pertinent examples likewise were later set forth in said referred to Application.

In that Application Ser. No. 411,103 it is further stated as follows:

"Employing the techniques of this invention, particularly that described in Example 1, the emulsions shown in the following Tables are continuously prepared. The column describing serial number and example refers to the example described in the serial number of the application specified. In each case the emulsions was prepared as stated in each example to yield the preformed emulsion and then the phases, including the filler where indicated, and emulsifiers are continuously added in the indicated ratios. For example, in Table I, Example 1, the preformed emulsion is prepared according to Example 74 of Ser. No. 286,877, now abandoned, and to this preformed emulsion, with appropriate stirring, a ratio of internal and extenal phase, including emulsifier, is added in approximately the same ratio as that found in the preformed emulsion. The ratio of external and internal phases is indicated in the Table.

TABLE I

| This Ex. | Serial Number | and | Ex. | External Phase | Internal Phase | Volume Ratio External-Internal Phase | | Emulsifier |
|---|---|---|---|---|---|---|---|---|
| 1 | 286,877 (now abandoned) | | 74 | water | Isooctane | 1/80 | .99 | Ex. 1 |
| 2 | " | | 75 | " | Kerosene | 0.75/10 | .93 | Ex. 66 |
| 3 | " | | 76 | " | Mineral Spirits | 1/50 | .98 | Ex. 67 |
| 4 | " | | Table VI | " | Kerosene | 1/50 | .98 | Ex. 18 |
| 5 | " | | Table VII | " | Kerosene | 1/65 | .98 | Ex. 6 |
| 6 | " | | Table VIII | " | Kerosene | 1/42 | .98 | Ex. 38 |
| 7 | " | | Table IX | " | Kerosene | 1/49.5 | .98 | Ex. 24 |
| 8 | " | | Table X | " | Kerosene | 1/48 | .98 | Ex. 65 |

SN 286,877 (now abandoned)
Emulsifier Ex. 1   n-decanol + PrO (1.96) + EtO (2.61)
Emulsifier Ex. 66  1,3-butanediol + BuO (3.0) + PrO (32.2) + EtO (16.6)
Emulsifier Ex. 67  Triethylene glycol + BuO (5.1) + PrO (30) + EtO (22)
Emulsifier Ex. 18  Crude phenol foots + EtO (1.75)
Emulsifier Ex. 6   n-decanol + PrO (3.67) + EtO (2.78)
Emulsifier Ex. 38  Phenol-aldehyde resin + PrO (1012M) + EtO (150.8M) moles/unit phenolic resin
Emulsifier Ex. 24  glycerine + BuO (2.52) + PrO (34.1) + EtO (21.0)
Emulsifier Ex. 65  Epichlorohydrin amine products + PrO (2.23) + EtO (2.93) + PrO (25.5) + EtO (40)

"All of the above ratios are parts by weight except where indicated. In relation to the phenolic resin the moles of alkylene oxide per unit of phenolic resin are specified i.e. the emulsifier of Ex. 38.

TABLE II

| This Ex. | Serial Number | & | Ex. | External Phase | Internal Phase | Volume Ratio External to Internal Phases | | Emulsifier | Filler |
|---|---|---|---|---|---|---|---|---|---|
| 1 | 302,177 | | 78 | water | kerosene | 1/30 | 0.97 | Ex. 1 Ex. 20 | Al(80G) |
| | (now abandoned and parent of S.N. 547,581, now U.S. Pat. No. 3,352,109) | | | | | | | | |
| 2 | 302,177 | | 79 | water | kerosene | 1/30 | 0.97 | Ex. 18 | Carbon Black (60g) |
| 3 | 302,177 | | 80 | water | kerosene | 1/30 | 0.97 | Table 1 Ex. 6 | Al(90g) |
| 4 | 302,177 | | 81 | water | kerosene | 1/30 | 0.97 | Table IV Ex. 40 | Al(80g) |
| 5 | 302,177 | | 82 | water | kerosene | 1/30 | 0.97 | Table IV Ex. 46 | Al(80g) |

SN 302,177 (now abandoned and parent of S.N. 547,581, now U.S. Pat. No. 3,352,109)
Emulsifier Ex. 1        n-decanol + PrO (1.96) + EtO (2.61)
Emulsifier Ex. 20       n-decanol + PrO (3.67)
Emulsifier Ex. 18       crude phenol foots + EtO (1.75)
Emulsifier Table I Ex. 6   n-decanol + PrO (3.67) + EtO (2.78)
Emulsifier Table IV Ex. 40  phenolic-aldehyde resin + PrO (1012M) + EtO (893.7M) moles/phenolic unit
Emulsifier Table IV Ex. 46  phenolic-aldehyde resin + PrO (848M) + EtO (487.5M) moles/phenolic unit "All of the above emulsifiers are parts by weight except where stated in relation to the phenolic resin where it is moles of alkylene oxide per unit of phenolic resin.

TABLE III

| This Ex. | Serial Number & Ex. | | External Phase | Internal Phase | Volume Ratio External to Internal Phases | | Emulsifier | Filler |
|---|---|---|---|---|---|---|---|---|
| 1 | 302,001 (now U.S. Pat. No. 3,396,537) | 87 | kerosene | hydrazine | 1/25 | 0.96 | Ex. 1 | — |
| 2 | 302,001 | Table I Test 3 | kerosene | hydrazine | 1/20 | 0.96 | Ex. 84 | Al(90g) |

SN 302,001 (now U.S. Pat. No. 3,396,537)
Emulsifier Ex. 1   n-decanol + PrO (1.96) + EtO (2.61)
Emulsifier Ex. 84  hexadecanol + PrO (1.2) + EtO (1.5) which is esterified with maleic anhydride.

"All of the parts specified above are parts by weight.

"The components of the oily and non-oily phases can be any of those specially designed in application Ser. No. 286,877 (now abandoned), Ser. No. 302,001 (now U.S. Pat. No. 3,396,537) and Ser. No. 302,177 (parent of Ser. No. 547,581, now U.S. Pat. No. 3,352,109) and the volume ratios inter se can be those specially designated in this application as well as in Ser. No. 286,877 (now abandoned), 302,001 (now U.S. Pat. No. 3,396,537) and Ser. No. 302,177 (parent of Ser. No. 547,581, now U.S. Pat. No. 3,352,109), for example, internal phases (either oily or non-oily) of from 50 - 99%.

"Any suitable emulsifier can be employed including those specifically mentioned in Ser. No. 286,877 (now abandoned), Ser. No. 302,001 (now U.S. Pat. No. 3,396,537) and Ser. No. 302,177 (parent of Ser. No. 547,581, now U.S. Pat. No. 3,352,109). Oxyalkylated emulsifiers are preferred but any suitable amount of emulsifier capable of preparing these emulsions can be employed, for example, in those amounts described in Ser. No. 286,877 (now abandoned), Ser. No. 302,001 (now U.S. Pat. No. 3,396,537) and Ser. No. 302,177 (Parent of Ser. No. 547,581, now U.S. Pat. No. 3,352,109). Although the amount of emulsifier present in the total emulsion can be from 0.05 - 5 volume percent, but preferably 0.2 - 3%, larger amounts can also be employed if desired. However, the economics generally restricts the amount employed to the ranges indicated.

"The emulsion can be a non-oily/oily emulsion, such as water-in-oil or an oily-non-oily emulsion such as oil-in-water. Other non-oily phases besides water can be employed such as hydrazine, glycols such as ethylene glycol, diethylene glycol, propyleneglycol, dipropylene glycol, etc. The preferred oily phase is a petroleum derived oily phase.

"The emulsions produced by this process may be employed for the uses specified in Ser. No. 286,877 (now abandoned), Ser. No. 302,001 (now U.S. Pat. No. 3,396,537) and Ser. No. 302,177 (parent of Ser. No. 547,581, now U.S. Pat. No. 3,352,109).

"This new, novel and useful process is a great improvement over current methods. Besides making it possible to produce emulsions on a continuous basis, it has the added advantage that the power requirements are much lower than for batch mixing. For example a 1½ gallon mixing chamber unit using a fractional horsepower motor was found to have an output of at least one quart per minute. This unit could produce over 100 gallons of emulsion in an eight hour shift. The output can be coupled to a filling machine and only as much emulsion as required for a run can be made. The unit can be stopped and restarted as desired. A one hundred gallon mixer to make the same emulsion on a batch basis would be much larger and would require a multi-horsepower stirrer and, furthermore, once a batch of emulsion is made it must all be used or wasted. If desired, solids may be incorporated into either phase."

Thus, any of the oily and non-oily materials, emulsifiers and techniques, etc. described in the above applications can be employed in preparing the emulsion of this invention.

Since these emulsions have been described in such great detail in the above applications, repetition herein is unnecessary.

The following examples are presented for purposes of illustration and not of limitation. Oxyalkylations were carried out by the general procedure described in U.S. Pat. No. 2,695,886, Example 1a.

Emulsifier A

An emulsifier was prepared by oxyalkylating 1,3-butanediol with 3.0 parts by weight of butylene oxide, 32.2 parts of propylene oxide and 16.6 parts of ethylene oxide in the order given.

Emulsifier B

An emulsifier was prepared by oxyalkylating triethyleneglycol with 5.1 parts by weight of butylene oxide, 30.0 parts of propylene oxide and 22 parts of ethylene oxide in the order given.

Emulsifier C

An emulsifier was prepared by oxyalkylated octyl phenol with 0.69 part by weight of ethylene oxide.

In addition non-oxyalkylated emulsifiers can also be employed.

The following Example illustates the preparation of a thixotropic water external-oil high internal phase emulsion.

EXAMPLE 1

Three quarts of water and 150 ml. of Emulsifier A were thoroughly mixed. One gallon of mineral oil was then added and mixed into this material until a smooth emulsion was formed. This premix was then placed into a 20 gallon open mixing vessel, equipped with an anchor type stirrer. With the stirrer revolving at about 200 rpm, additional mineral oil was added until a total of ten gallons of mineral oil had been mixed in. The result was a white, highly thixotropic, oil-in-water emulsion.

The following example illustrates the preparation of a thixotropic water external-oil high internal phase emulsion.

EXAMPLE 2

A two inch diameter, Viking pump, driven by an electric motor at 805 rpm, was equipped with an eight foot flexible hose on the outlet and a similar flexible hose on the inlet. The ends of the two hoses were placed in a 50 gallon, open head, steel drum. With this arrangement, material could be pumped out of the drum, through the pump, and back into the drum.

One gallon of water and one pint of Emulsifier B were mixed together and placed in the steel drum. While this material was circulated by the pump, mineral oil was slowly added to the intake of the pump. In about 15 minutes, 50 gallons of mineral oil had been added and the result was a thick, white, jelly-like emulsion.

The following example illustrates the preparation of an oil external-high internal water phase thixotropic emulsion.

EXAMPLE 3

A two inch diameter, Viking pump, driven by an electric motor at 850 rpm, was equipped with an eight foot flexible hose on the outlet and a similar flexible hose on the inlet. The ends of the two hoses were placed in a 50 gallon, open head, steel drum. With this arrangement, material could be pumped out of the drum, through the pump, and back into the drum.

One gallon of mineral oil and one pint of Emulsifier C were mixed together and placed in the steel drum. While this material was circulated by the pump, water was slowly added to the intake of the pump. In about 15 minutes, 50 gallons of water had been added and the result was a thick, while, jelly-like emulsion.

EXAMPLE 4

Small laboratory batches of emulsions may be made in a kitchen-type mixer such as the Model C3 Kitchen Aid Mixer manufactured by the Hobart Manufacturing Company. This mixer uses a two quart glass mixing bowl and a wire beater with a planetary motion. A typical water-on-oil high internal phase ratio cosmetic base cream was made as follows:

EXAMPLE 5

6 ml. of light mineral oil, 2 ml. of lanolin, 1 ml. of the emulsifier described in Example 1 of U.S. Pat. No. 3,352,109 and 1 ml. of the emulsifier of Example 21 of U.S. Pat. No. 3,352,109 were placed in the mixer bowl of the Kitchen Aid Mixer. With the mixer speed at No. 3, 5 ml. increments of distilled water were added mixing thoroughly between additions, until a total of 50 ml. of water had been added. Additional water was then added slowly until a total of 190 ml. of distilled water had been added. The result was a thick, creamy, white stable emulsion containing 95 volumes of distilled water emulsified in 5 volumes of the oily external phase. An emulsion of this type will function as a base cream for a variety of formulations. For instance, an appropriate amount of ultra violet absorber such as dipropylene glycol salicylate may be added to produce a sunburn preventive cream. Alternatively, an insect repellent such as dimethyl formamide or diethyl toluamide may be added. Perfume oils and coloring ingredients may be incorporated to suit particular purposes. When a particular active ingredient is to be incorporated into the oily phase it may be necessary to modify the emulsifier combination to obtain optimum properties. Techniques for selection of emulsifiers are described in our aforestated U.S. Patents and Applications. If desired, suitable pigments may be dispersed in the aqueous phase prior to emulsification to give the formulations opacity and to match skin tones. Water soluble ingredients can be dissolved in the internal phase.

For example, specific formulations may be prepared as follows:

EXAMPLE 6

A sunburn preventive cream is produced following the procedures of the previous example. The external phase consists, for example, of a light mineral oil in which are dissolved approximately 0.1 to 3%, by weight of said light mineral oil, of an ultra-violet screening agent, dipropylene glycol salicylate, and approximately 1 to 10%, by weight of said light mineral oil, of oil soluble emulsifier described in Example 1 of U.S. Pat. No. 3,352,109. The internal phase consists either of water or of water containing a small amount of an emollient, glycerine. The water phase is additionally buffered so as to be isotonic with human skin. The actual emulsion is made by any one of the techniques set forth in any of the previous examples. For example, the external phase is placed in a Hobart type mixer and the internal phase is added slowly with the mixer speed set at an intermediate level. Alternatively, the emulsion is produced by recirculating the external phase through a pump as described in the previous example, while introducing the internal phase slowly into the intake of the pump. Preferably, for commercial production, the internal phase and the external phase are introduced simultaneously into the mixing chamber of a continuous emulsifying device as described in abandoned Application Ser. No. 411,103 and its continuation-in-part Application Ser. No. 753,340, now U.S. Pat. No. 3,565,817.

EXAMPLE 7

By exactly the same procedures as set forth in Example 6, a useful insect repellent formulation is made by substituting approximately 1 to 10%, by weight of said light mineral oil, of an oil soluble insect repellent, diethyl toluamide, in place of the ultra-violet screening agent. The manufacturing procedure is that of Example 6.

A typical example of a nutritive emulsion is as follows:

EXAMPLE 8

The external phase is an edible oil, corn oil or salad oil. Specifically, the procedure and amounts and the emulsifier set forth in Example 3 herein are used. To the edible oil, corn oil or salad oil, is added food grade emulsifier C. Water is the internal phase. A high-internal-phase-ratio water in oil emulsion is thereby produced. The formed emulsion has the general properties of mayonnaise or salad dressing with the advantage that the caloric content is very low making it particularly applicable for diets where the control of caloric intake is desired. Another particular advantage is that water soluble flavoring agents can be incorporated in the internal phase. Also, insoluble food flavoring materials such as mustard or turmeric can be added to the aqueous phase to produce a final formulation which is homogeneous and non-settling.

| Example 8a | |
|---|---|
| External phase | |
| corn oil | one gallon |
| Emulsifier C | one pint |
| Internal phase | |
| water | 50 gallons |
| Example 8b | |
| External phase | |
| salad oil | one gallon |
| Emulsifier C | one pint |
| Internal phase | |

| | |
|---|---|
| water | 50 gallons |

EXAMPLE 9

The base cream of Example 5 is made into an antiperspirant cream by using as the internal phase a 15% aqueous solution of aluminum chlorohydrate.

EXAMPLE 10

The base cream of Example 5 is made into an antiperspirant cream by using as the internal phase a 20% aqueous solution of aluminum sulfate with 10%, by weight of the internal phase, titanium dioxide suspended therein.

EXAMPLE 11

A leg make-up or "liquid stocking" is made as follows:

| Place in Hobart mixer | |
|---|---|
| light mineral oil emulsifier | 1 gallon |
| emulsifier of Example 1 of U.S. Pat. No. 3,352,109 | ½ pint |
| emulsifier of Example 21 of U.S. Pat. No. 3,352,109 | ½ pint |
| Add slowly, while stirring, a mixture made by milling together | |
| Water | 8 gallons |
| White powder base | 10 pounds |
| Concentrated ochre | 1 dram |
| Geranium lake | 2 drams. |

EXAMPLE 12

A waterless hand cleaner is made by feeding to the mixing chamber of the continuous emulsifier as described in U.S. Pat. No. 3,565,817 the following, one part of external phase for each 4 – 6 parts of internal phase:

| External phase | |
|---|---|
| Odorless kerosene | 6 parts by volume |
| Diglycol oleate | 2 parts by volume |
| Emulsifier of Example 1 of U.S. Pat. No. 3,352,109 | 1 part by volume |
| Emulsifier of Example 21 of U.S. Pat. No. 3,352,109 | 1 part by volume |
| Internal phase | |
| Water | 75 parts by volume |
| Glycerine | 5 parts by volume |
| Perfume | 10 parts by volume. |

The HIPR (high-internal-phase-ratio) emulsions of this invention may be employed in numerous individual cosmetic preparations of which the more important ones can be grouped in the following categories: (1) Creams, including cold creams, vanishing creams, absorption base creams, and creams for special purposes such as suntan creams, depilatories, deodorants, etc.; (2) Lotions (like the creams, these may be specifically formulated for a variety of purposes); (3) Make-up and facial preparations; (4) Shampoos, hair-waving preparations, and other preparations for the hair; (5) Shaving preparations; (6) Dentifrices; (7) Bath preparations; (8) Toilet soaps, including special cleansers for persons with sensitive skin; (9) Hand-cleaning compositions, including industrial hand cleaners, hand soaps for use in dispensers at public lavatories, etc.; (10) Nutritive compositions including puddings, pie fillings, imitation whipped cream, low calorie sherberts, etc.

Categories (8) and (9) verge closely on the fields of medical uses and janitors' supplies, respectively. This is scarcely surprising in view of the function and action of emulsions in such products. Many preparations which might be considered primarily as cosmetics have actual beneficial values for the skin and could therefore also be classed as dermatological remedies. The reverse is, of course, also true. A dermatological remedy which will aid in restoring health to a disordered skin and which is harmless enough to be dispensed without a prescription may, in fact, be sold as a cosmetic at cosmetic counters.

As is quite evident, a wide variety of thixotropic emulsions are useful in this invention. It is, therefore, not only impossible to attempt a comprehensive catalogue of such compositions, but to attempt to describe the invention in its broadest aspects in terms of specific chemical names for the components of such emulsions would be too voluminous and unnecessary since one skilled in the art could be following the description of the invention herein prepare an appropriate emulsion. This invention encompasses the use of thixotropic and other pseudo plastic fluids in cosmetic and pharmaceutical compositions and the individual components of such fluids are important only in the sense that they affect this function. To precisely define each specific useful phase of the emulsion and emulsifier in light of the present disclosure would merely call for chemical knowledge within the skill of the art in a manner analogous to a mechanical engineer who prescribes in the construction of a machine the proper materials and the proper dimensions thereof. From the description in this specification and with the knowledge of a chemist, one will know or deduce with confidence the applicability of specific phases of the emulsions and emulsifiers suitable for this invention by applying them in the process set forth herein. In analogy to the case of a machine, wherein the use of certain materials of construction or dimensions of parts would lead to no practical useful result, various materials will be rejected as inapplicable where others would be operative. I can obviously assume that no one will wish to use a useless emulsion nor will be misled because it is possible to misapply the teachings of the present disclosure to do so. Thus, any thixotropic emulsion can perform the function stated herein can be employed. Analogously other thixotropic or pseudo-plastic fluids besides emulsions can be employed.

Having thus described my invention what I claim as new and desire to obtain by Letters Patent is:

1. A pharmaceutical thixotropic high internal phase ratio emulsion characterized by the presence of a pharmaceutical agent therein, said thixotropic high internal phase ratio emulsion having the characteristics of a solid when at rest and the characteristics of a liquid when a force is exerted on it, the emlsion having (1) an emulsifying agent, (2) a pharmaceutically acceptable emulsifiable oil, and (3) a liquid pharmaceutically acceptable non-oil, said thixotropic high internal phase ratio emulsion being selected from the group consisting of (1) an oil-in-non-oil emulsion and (2) a non-oil-in-oil emulsion, the internal phase of said emulsion being present in an amount of at least 80% by volume of the emulsion.

2. The composition product of claim 1 wherein the non-oil is water.

3. The composition of claim 2 wherein the internal phase is present in an amount of at least 90% by volume of the emulsion.

4. The composition product of claim 3 wherein the internal phase is present in an amount of at least 95% by volume of the emulsion.

5. The composition product of claim 1 wherein the oil comprises mineral oil.

6. The composition product of claim 1 wherein the oil is a mixture of mineral oil and lanolin.

7. The composition product of claim 2 wherein the oil comprises mineral oil.

8. The composition product of claim 2 wherein the oil is a mixture of mineral oil and lanolin.

9. The composition product of claim 3 wherein the oil comprises mineral oil.

10. The composition product of claim 3 wherein the oil is a mixture of mineral oil and lanolin.

* * * * *